(12) United States Patent
Denayer et al.

(10) Patent No.: US 7,435,865 B2
(45) Date of Patent: Oct. 14, 2008

(54) METHOD FOR SEPARATING HYDROCARBONS AND USE OF A ZEOLITE THEREFOR

(75) Inventors: Joeri Denayer, Sint-Laureins-Berchem (BE); Refik Ocakoglu, Brussels (BE); Gino Baron, Tervuren (BE)

(73) Assignee: Vrije Universiteit Brussel, Brussel (BE)

( * ) Notice: Subject to any disclaimer, the term of this patent is extended or adjusted under 35 U.S.C. 154(b) by 309 days.

(21) Appl. No.: 10/568,723

(22) PCT Filed: Aug. 17, 2004

(86) PCT No.: PCT/EP2004/009216

§ 371 (c)(1),
(2), (4) Date: Feb. 17, 2006

(87) PCT Pub. No.: WO2005/016857

PCT Pub. Date: Feb. 24, 2005

(65) Prior Publication Data

US 2006/0241330 A1    Oct. 26, 2006

(30) Foreign Application Priority Data

Aug. 18, 2003  (WO) .................. PCT/EP03/09133

(51) Int. Cl.
```
C07C 7/12      (2006.01)
C07C 7/13      (2006.01)
C07C 7/00      (2006.01)
C07C 5/13      (2006.01)
B01D 53/02     (2006.01)
B01D 15/00     (2006.01)
B01D 15/08     (2006.01)
```
(52) U.S. Cl. .................. 585/820; 585/802; 585/738; 585/734; 585/736; 585/822; 585/825; 585/830; 95/90; 203/41; 208/310 R; 208/310 Z; 210/656

(58) Field of Classification Search .................. 585/802, 585/820, 738, 734, 736, 822, 825, 830; 95/90; 203/41; 208/310, 310 R, 310 Z; 210/656
See application file for complete search history.

(56) References Cited

U.S. PATENT DOCUMENTS

| | | | | |
|---|---|---|---|---|
| 4,855,529 A | * | 8/1989 | Stem et al. | 585/737 |
| 5,146,029 A | * | 9/1992 | Bundens et al. | 585/533 |
| 5,321,194 A | * | 6/1994 | Apelian et al. | 585/671 |
| 5,352,354 A | * | 10/1994 | Fletcher et al. | 208/89 |
| 6,069,289 A | * | 5/2000 | Dandekar et al. | 585/820 |
| 6,156,950 A | * | 12/2000 | Ragil et al. | 585/802 |
| 6,281,406 B1 | | 8/2001 | Cain | |
| 6,353,144 B1 | * | 3/2002 | Ragil et al. | 585/825 |
| 6,407,305 B1 | * | 6/2002 | Sohn | 585/820 |
| 6,734,133 B1 | * | 5/2004 | Weisbeck et al. | 502/119 |
| 2003/0196931 A1 | * | 10/2003 | Houzvicka et al. | 208/65 |

FOREIGN PATENT DOCUMENTS

EP    0 384 540    8/1990

OTHER PUBLICATIONS

International Search Report dated Feb. 1, 2005.

* cited by examiner

*Primary Examiner*—Walter D. Griffin
*Assistant Examiner*—Huy-Tram Nguyen
(74) *Attorney, Agent, or Firm*—Knobbe, Martens, Olson & Bear, LLP

(57) ABSTRACT

A method for separating a mixture of hydrocarbons into fractions enriched in linear, mono-branched, or multi-branched hydrocarbons is disclosed. In particular, mono-branched alkanes are separated from a mixture of alkanes containing multi-branched, mono-branched and linear alkanes, by selectively adsorbing the mono-branched alkanes on a zeolitic adsorbent. The zeolitic adsorbent MCM-22 is particularly suitable for carrying out the method.

20 Claims, 6 Drawing Sheets

METHOD FOR SEPARATING HYDROCARBONS AND USE OF A ZEOLITE THEREFOR

RELATED APPLICATIONS

This application is the U.S. National Phase under 35 U.S.C. § 371 of International Application PCT/EP2004/009216, filed Aug. 17, 2004, which claims priority of PCT/EP03/09133, filed Aug. 18, 2003.

FIELD OF THE INVENTION

The present invention relates to the field of hydrocarbon separation. More specifically, the present invention relates to a hydrocarbon separation process utilizing a zeolitic adsorbent, to preferentially adsorb mono-branched hydrocarbons by said adsorbent from a mixture with linear, di- and multi-branched hydrocarbons.

BACKGROUND OF THE INVENTION

The increasing demand for high purity chemicals requires development of hyperselective separation processes. Compared to distillation, separation by adsorption on solid surfaces allows achieving much higher selectivities (Ruthven, 1984; John Wiley and Sons: New York).

Among the broad range of industrial adsorbents, zeolites represent a particular family. Whereas with conventional materials, discrimination results from specific energetic interactions between molecules and the adsorbent surface, the selectivity of zeolites arises from the subtle matching of size and shape of guest molecules and zeolite micropores (Chen et al, 1989; Marcel Dekker, Inc.: New York).

Zeolitic materials, both natural and synthetic, have been demonstrated in the past to have catalytic properties for various types of hydrocarbon conversion. Certain zeolitic materials are ordered, porous crystalline aluminosilicates having a definite crystalline structure as determined by X-ray diffraction, within which there are a large number of smaller cavities, which may be interconnected by a number of still smaller channels or pores. These cavities and pores are uniform in size within a specific zeolitic material. Since the dimensions of these pores are such as to accept for adsorption molecules of certain dimensions while rejecting those of larger dimensions, these materials have come to be known as "molecular sieves" and are utilized in a variety of ways to take advantage of these properties.

Various types of zeolites can be used for separating various hydrocarbon types such as aromatics, alkanes or alkenes, from each other. Specific zeolites can be utilized which have been base exchanged to allow the various cations to be utilized advantageously in performing a predetermined selective adsorption of a hydrocarbon type.

In common industrial adsorptive separation processes using zeolites, straight chain alkanes are adsorbed into the pores of the zeolites, while the more branched alkanes are excluded from entering the pores. Adsorption of branched molecules is essentially restricted by the small pore size of the zeolites. Hence, mono- and multi-branched alkanes are not separated from each other. Therefore, there remains a need in the art for providing a method for separating the more bulky, mono-branched molecules from the multi-branched and the linear molecules.

U.S. Pat. No. 6,069,289 describes a process to separate multimethyl-branched alkanes from a mixture of multimethyl-branched alkanes, monomethyl-branched alkanes and normal alkanes. The adsorbent particles in this process have a selectivity order from normal alkanes to monomethyl-branched alkanes further to multimethyl-branched alkanes.

US 20002/0045793 discloses a process for separating multi-branched alkanes comprised in a hydrocarbon feed using at least one zeolitic adsorbent. The adsorbent preferably adsorbs linear alkanes, to lesser extent mono-branched alkanes and finally only minor amounts of multi-branched alkanes, naphthenic compounds and aromatic compounds.

U.S. Pat. No. 5,107,052 describes the selective adsorption of multi-branched alkanes on SAPO-5, $AlPO_4$-5, SSZ-24, MgAPO-5 or MAPSO-5 zeolites. These zeolites are aluminophosphates, except SSZ-24 which is a all-silica zeolite that is isostructural with $AlPO_4$-5, and characterized in that they have pores large enough to admit all components of a mixture of linear, mono- and di-branched alkanes, and selectively adsorb di-methyl alkanes but no mono-methyl and normal alkanes.

The present invention aims to provide an improved separation method, which favors adsorption of the mono-branched hydrocarbons, to lesser extent linear hydrocarbons and finally only minor amounts of di- and multi-branched hydrocarbons. Even more in particular, it is an object of the present invention to provide an improved method that favors adsorption of mono-branched alkanes, to lesser extent linear alkanes and finally only minor amounts of di- and multi-branched alkanes.

Another object of the present invention is to provide an improved method for separating mixtures of hydrocarbons into fractions enriched in linear, mono-branched or multi-branched hydrocarbons. Even more in particular, it is the object of the present invention to provide an improved method for separating mixtures of mono-branched alkanes into fractions enriched in linear, mono-branched or multi-branched hydrocarbons.

The present invention has the object to provide such separation methods using zeolite-based adsorbents to preferentially adsorb mono-branched hydrocarbons.

SUMMARY OF THE INVENTION

The present invention is based on preferential adsorption of certain particular zeolitic materials towards mono-branched hydrocarbons compared to their linear counterparts. In particular, the present invention describes a zeolite-based separation method showing pronounced preference for adsorbing mono-branched hydrocarbon molecules, occurring at all degrees of zeolite pore occupancy and caused by an entropic effect.

It has surprisingly been discovered that the use of a particular type of zeolitic adsorbent, which is described into detail below, has a beneficial effect on the adsorption of mono-branched alkanes comprised in a mixture of alkanes. In particular, said zeolitic adsorbents were shown to selectively adsorb mono-branched alkanes from a mixture of multi-branched, mono-branched and linear alkanes. The zeolitic adsorbent used in the process of the invention combines good selectivity with optimum adsorption capacity of mono-branched alkanes. It should be noted that this surprising effect is unexpected and not obvious. In fact, adsorption in zeolites should normally prefer multi-branched moieties in the hydrocarbon structure. The zeolites of the present invention demonstrate a clear selective adsorption for the mono-branched hydrocarbons.

In a first aspect, the invention relates to a method for separating mixtures of hydrocarbons into fractions of linear, mono-branched and multi-branched hydrocarbons.

In another aspect, the invention relates to a method for separating mono-branched hydrocarbons e.g. from a mixture of hydrocarbons comprising bringing said mixture into contact with at least one adsorbent, thereby allowing the selective adsorption of said mono-branched hydrocarbons, preferably alkanes by said adsorbent, and desorbing said mono-branched hydrocarbons, preferably alkanes from said adsorbent, thereby allowing to selectively separate said mono-branched hydrocarbons, preferably alkanes.

The terms "separating" and "enriching" are used as synonyms herein and are to be understood as referring to a separation of 100% as well as to any gradation of separation providing an increased enrichment of a certain fraction and comprised between 100 and 90%, or 90 and 80%, or 80 and 70% or 70 and 60% or 60 and 50% of separation. It will be clear that also a gradation of separation lower than 50% is encompassed by this definition of separating.

In a second aspect, the invention relates to the use of at least one adsorbent, preferably a zeolitic adsorbent, for separating mono-branched hydrocarbons and preferably alkanes e.g. from a mixture of hydrocarbons and preferably from a mixture of alkanes. Said adsorbent has a selectivity order from mono-branched to linear further to multi-branched hydrocarbons. This means that said adsorbent preferentially adsorbs mono-branched, to a lesser extent linear hydrocarbons and finally to an even lower extent multi-branched hydrocarbons.

The present invention provides in particular a novel method, based on zeolitic adsorbents, for separating mono-branched alkanes from a mixture with other alkanes and in particular with multi-branched and linear alkanes. Unexpectedly, and in contrast to expectations in the art, mono-branched alkanes are relatively more adsorbed by the zeolitic material used in the present invention than linear or multi-branched alkanes.

Furthermore, it was demonstrated that the selective uptake of mono-branched alkanes from mixtures with other alkanes such as linear and multi-branched alkanes occurs at all degrees of zeolite loading. In particular, the applicant showed a higher retention of mono-branched alkanes compared to its linear counterparts, at all degrees of pore occupancy of the zeolitic material, also at very low occupancy. This feature is important because it allows operating the separation process in a broad range of operating conditions, in gas, vapor or liquid phase.

In addition, the applicants showed that selective adsorption is caused by entropic effects. According to the present invention, it was demonstrated that mono-branched alkanes loose less freedom upon adsorption on zeolites compared to linear alkanes and are thus more preferably adsorbed on the zeolitic material compared to linear alkanes. Such behavior is completely unexpected and essentially due to the particular shape and size of the cavities in the zeolitic material. The very peculiar adsorption behavior of the zeolitic material is ascribed to the unique shape and size of the cavities of the zeolitic material, which are very well accommodating the mono-branched alkanes, in such a way that they retain more freedom than the linear isomers. Shape and size of the cavities of the zeolitic material used according to the present invention is described into more detail below.

In terms of chemical utility, the present invention provides a method for preferentially adsorbing mono-branched hydrocarbons and preferably alkanes from a mixture with multi-branched and linear hydrocarbons and preferably alkanes, that can be used to supply relatively purified components to other processing units, for instance in the petrochemical or other industries.

Other objects and advantages of the present invention will become apparent from the following detailed description taken in conjunction with the accompanying figures and examples.

DETAILED DESCRIPTION OF THE FIGURES

Figure 7:
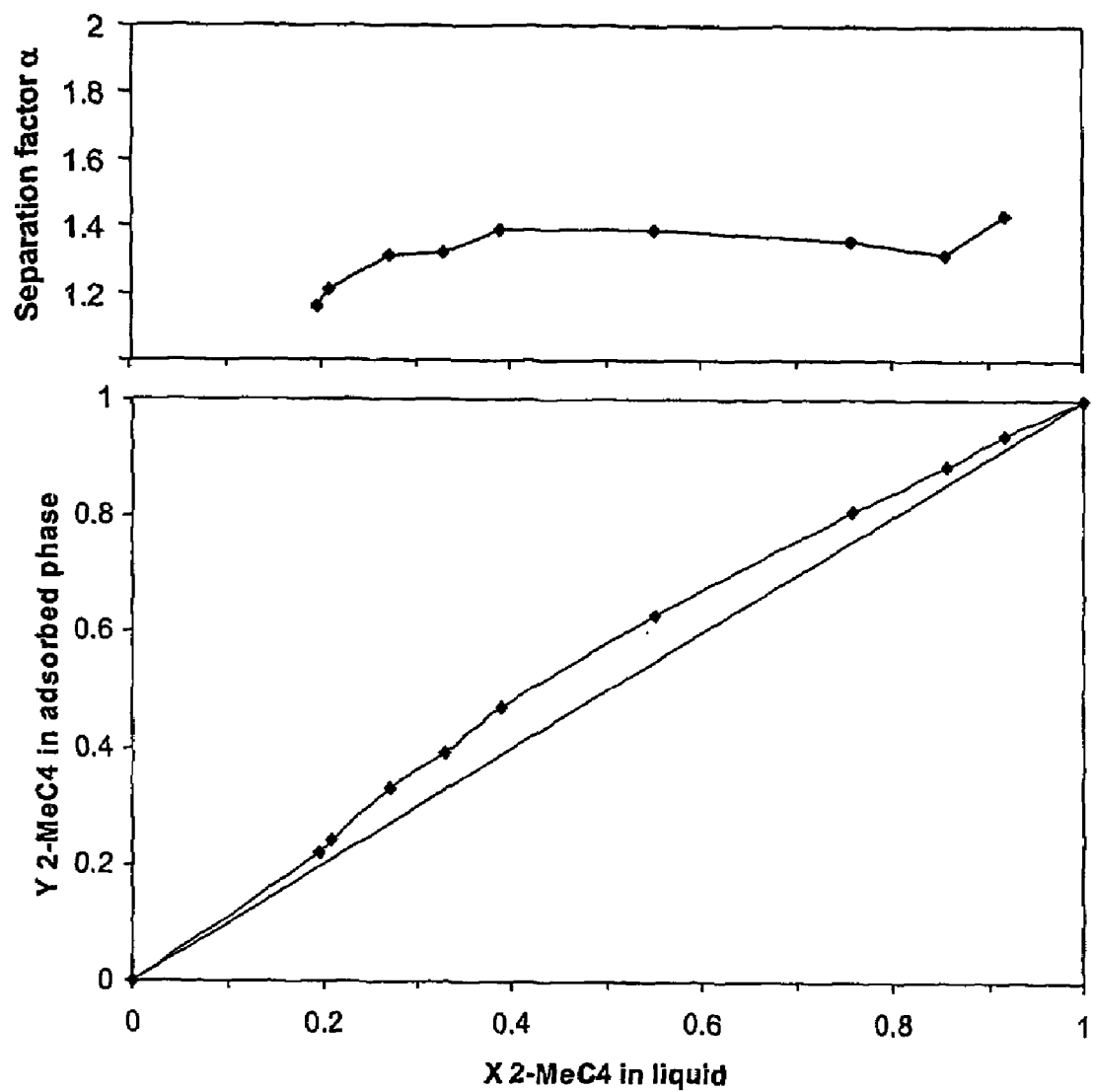

FIG. 7 provides a selectivity curve and separation factor for the liquid phase adsorption of a pentane/2-methylbutane mixture on MCM-22 (X 2-MeC4: mole fraction of 2-methylbutane in the liquid phase; Y 2-MeC4: mole fraction of 2-methylbutane in the adsorbed phase).

Figure 8:
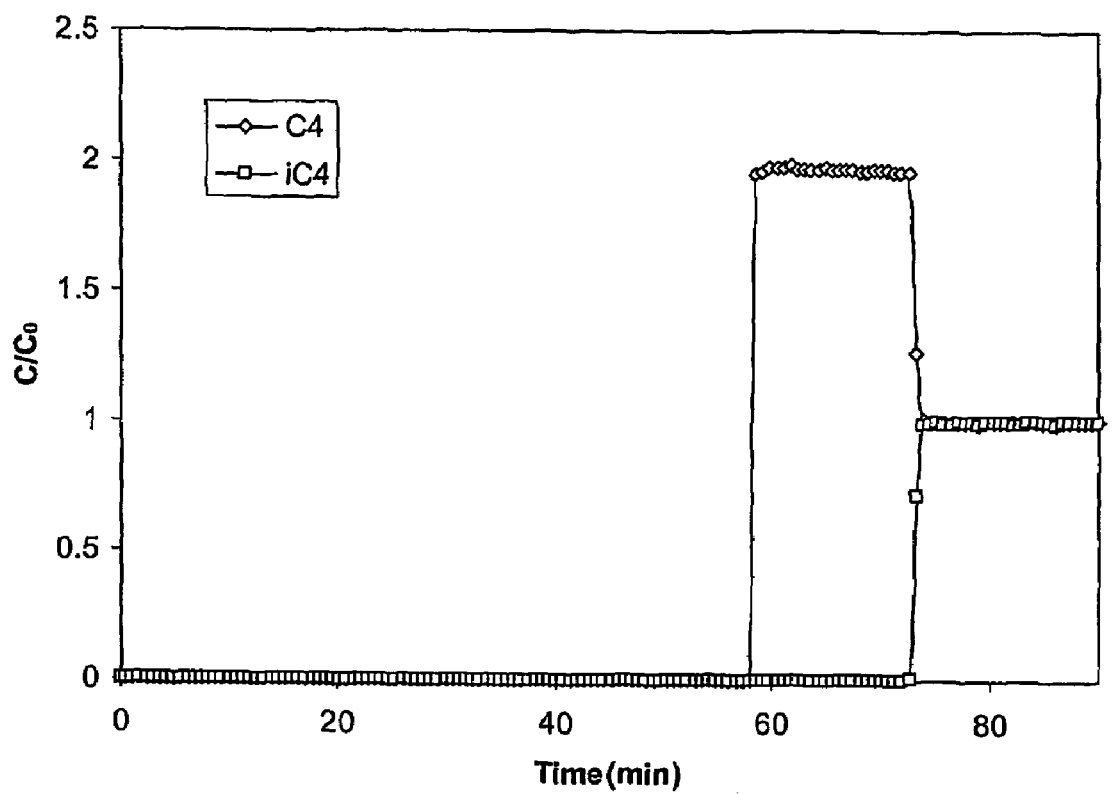

FIG. 8 shows the breakthrough profile of an equimolar butane/iso-butane mixture diluted in Helium obtained on MCM-22 column at 130° C. and a total hydrocarbon pressure of 0.2 bar.

Figure 9:
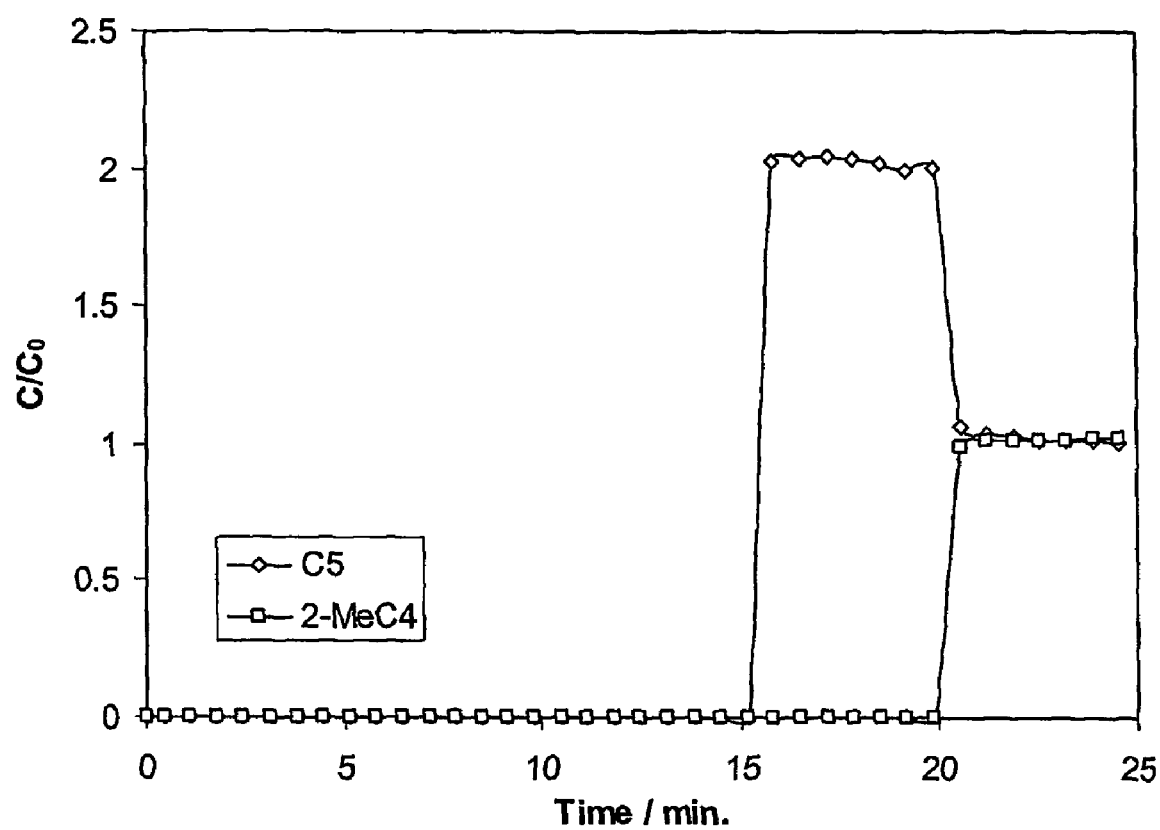

FIG. 9 shows the breakthrough profile of an equimolar pentane/2-methyl-butane mixture diluted in Helium obtained on MCM-22 column at 130° C. and a total hydrocarbon pressure of 0.2 bar.

DETAILED DESCRIPTION OF THE INVENTION

In a first aspect, the present invention provides an improved method for separating mixtures of hydrocarbons into fractions of linear, mono-branched and multi-branched hydrocarbons. This method is based on the use of an adsorbent having a selectivity order from mono-branched hydrocarbons to linear hydrocarbons further to multi-branched hydrocarbons. The method comprises the steps of:
  a. bringing said mixture into contact with at least one adsorbent, said adsorbent having a selectivity order from mono-branched to linear further to multi-branched hydrocarbons,
  b. separating a stream enriched in multi-branched hydrocarbons from said adsorbent, thereby allowing to separate said multi-branched hydrocarbons,
  c. desorbing the linear hydrocarbons from said adsorbent, thereby allowing to separate said linear hydrocarbons, and
  d. desorbing said mono-branched alkanes from said adsorbent, thereby allowing to separate said mono-branched hydrocarbons.

The term "a selectivity order" means that said adsorbent preferentially adsorbs mono-branched, to a lesser extent linear hydrocarbons and finally to an even lower extent multi-branched hydrocarbons.

Desorption of the adsorbed mono-branched hydrocarbons can be achieved using known techniques such as temperature increase, pressure decrease or desorption using a suitable desorbent, or a combination of these.

In a preferred embodiment, the linear hydrocarbons are first desorbed, and subsequently, the mono-branched hydrocarbons are desorbed. In another preferred embodiment, the hydrocarbons are desorbed from the adsorbent using a suitable desorbent. Preferably, a first desorbent capable of desorbing the linear hydrocarbons but incapable of desorbing the mono-branched hydrocarbons is used for desorbing the linear hydrocarbons, and a second desorbent capable of desorbing the mono-branched hydrocarbons from said adsorbent is used for desorbing the mono-branched hydrocarbons. These operations can be carried out in the various forms of batch or cyclic processes known to those skilled in the art (PSA, TSA, chromatography, SMB).

The term "hydrocarbons" as used herein refers to non-aromatic alkanes or alkenes, preferably to $C_4$ to $C_{20}$ alkanes or alkenes, more preferably to $C_4$ to $C_{18}$ alkanes or alkenes, more preferably to $C_4$ to $C_{10}$ alkanes or alkenes, and even more preferred to $C_4$ to $C_8$ alkanes or alkenes, and even more preferred to $C_4$ to $C_6$ alkanes or alkenes. In a preferred embodiment, the hydrocarbons are alkanes.

The term "mixture of hydrocarbons" as used herein is meant to encompass linear, mono-branched, di-branched, tri-branched, and higher branched alkanes or alkenes or any combinations thereof as defined herein. Preferably, the mixture of hydrocarbons is meant to refer to mixtures of linear, mono-branched, di-branched, tri-branched, and higher branched alkanes.

The term "linear hydrocarbons" or "normal hydrocarbons" or "n-hydrocarbons" or a similar term, as used herein is self-explanatory and is meant to encompass those hydrocarbons that are essentially defined in the art as straight-chained hydrocarbons.

The term "mono-branched hydrocarbons" as used herein, is meant to include those hydrocarbons that contain only one alkyl substitution on the chain in order to form a non-straight chained configuration. Preferably, a single methyl or higher alkyl group is substituted on the chain.

The term "multi-branched hydrocarbons", as used herein, is defined as any hydrocarbons having more than one alkyl substitution of a carbon atom or atoms on the chain to form a non-straight chained configuration. Included in this definition are the dual (di-branched), triple (tri-branched), and even higher alkyl-branched hydrocarbons.

In a preferred embodiment, said hydrocarbons are alkanes and the present invention relates to a method for separating mixtures of alkanes into fractions of linear, mono-branched and multi-branched alkanes.

In another aspect, the present invention provides an improved method for separating mono-branched hydrocarbons from a mixture of hydrocarbons using an adsorbent. More in particular, the present invention provides an improved method for separating mono-branched alkanes from a mixture of alkanes using an adsorbent.

The method involves the selective adsorption of mono-branched alkanes on a particular type of zeolitic material, at the expense of other types of alkanes, and in particular linear alkanes, in a mixture. The method according to the invention comprises bringing said mixture into contact with at least one adsorbent, whereby said mono-branched alkanes are selectively adsorbed by said adsorbent. Then the mono-branched alkanes can be desorbed from said adsorbent, thereby allowing separating said mono-branched alkanes. Desorption of the adsorbed mono-branched alkanes can be achieved using known techniques such as temperature increase, pressure decrease or desorption using a suitable desorbent, or a combination of these, both in batch and continuous or cyclic processes such as TSA, PSA, SMB, chromatography.

As used herein, the term "alkanes" refers to non-aromatic, saturated hydrocarbons with the general formula $C_nH_{(2n+2)}$, wherein n is from 4 to 20, preferably from 4 to 10, more preferably from 4 to 8, or more preferably from 4 to 6.

The term "linear alkanes" or "normal alkanes" or "n-alkanes" or a similar term, as used herein is self-explanatory and is meant to encompass those alkanes that are essentially defined in the art as straight-chained alkanes.

The term "mono-branched alkanes" as used herein, is meant to include those alkanes that contain only one alkyl substitution on the chain in order to form a non-straight chained configuration. Preferably, a single methyl or higher alkyl group is substituted on the chain. Examples of suitable mono-branched alkanes that can be separated according to the invention include, but are not limited, to 2-methylbutane, 2-metylpentane, 3-methylpentane, 2-methylhexane, 3-methylhexane, 2-methylheptane, 3-methylheptane, 4-ethylheptane, 3-ethyl-pentane etc. . . .

The term "multi-branched alkanes", as used herein, is defined as any alkane having more than one alkyl substitution of a carbon atom or atoms on the chain to form a non-straight chained configuration. Included in this definition are the dual (di-branched alkanes), triple (tri-branched alkanes), and even higher alkyl-branched alkanes. Examples of multi-branched alkanes according to the invention include, but are not limited to, 2,2-dimethylbutane, 2,3-dimethylbutane, 2,2-dimethylpentane, 3,3-dimethylpentane, 2,3-dimethylpentane, 2,4-dimethylpentane, 2,2,3-trimethylbutane, 2,2-dimethylhexane, 3,3-dimethylhexane, 2,3-dimethylhexane, 3,4-dimethylhexane, 2,4-dimethylhexane, 2,5-dimethylhexane, 2,2,3-trimethylpentane, 2,3,3-trimethylpentane, or 2,3,4-trimethylpentane.

As used herein the term "alkenes" refers to non-aromatic, unsaturated hydrocarbons having one or more double carbon-carbon bonds and having general formula $C_nH_{(2n+2)-2x}$, wherein x is the number of double bonds and n is from 4 to 20, preferably from 4 to 10, more preferably from 4 to 8, or more preferably from 4 to 6.

The term "linear alkenes" or "normal alkenes" or "n-alkenes" or a similar term, as used herein is self-explanatory and is meant to encompass those alkenes that are essentially defined in the art as straight-chained alkenes.

The term "multi-branched alkenes", as used herein, is defined as any alkene having more than one alkyl substitution of a carbon atom or atoms on the chain to form a non-straight chained configuration. Included in this definition are the dual (di-branched alkenes), triple (tri-branched alkenes), and even higher alkyl-branched alkenes.

The term "alkyl", alone or in combination, means straight and branched chained saturated hydrocarbon radicals containing from 1 to 20 carbon atoms, preferably from 1 to 10, more preferably from 1 to 8 carbon atoms, or more preferably from 1 to 6 carbon atoms. Examples of such radicals include methyl, ethyl, n-propyl, isopropyl, n-butyl, isobutyl, sec-butyl, tert-butyl, 2-methylbutyl, pentyl, iso-amyl, hexyl, 3-methylpentyl, octyl and the like.

The term "mixture of alkanes" as used herein is meant to encompass linear, mono-branched, di-branched, tri-branched, and higher branched alkanes as defined herein.

In another preferred embodiment, the invention relates to a method for separating mono-branched hydrocarbons from a mixture of hydrocarbons by preferentially adsorbing mono-branched hydrocarbons onto said adsorbent. In a more preferred embodiment, the invention relates to a method for separating mono-branched alkanes from a mixture of alkanes by preferentially adsorbing mono-branched alkanes from said mixture of alkanes onto said adsorbent. The term "preferentially" as used herein refers to the adsorption of a substantially larger amount of mono-branched hydrocarbons, in particular alkanes, than other hydrocarbons, in particular alkanes that occur in the mixture. Preferably, the selectivity α for mono-branched alkanes, defined as $\alpha=(X_{MB}/(1-X_{MB}))/(Y_{MB}/(1-Y_{MB}))$ where $X_{MB}$ and $Y_{MB}$ are, respectively, the mole fractions of the mono-branched alkanes in the adsorbed phase and in the bulk phase at thermodynamical equilibrium, is at least 1.1, more preferably at least 1.2 and even more preferred higher than 1.3.

In an embodiment, the adsorbent according to the present invention is a zeolitic adsorbent. Said "zeolitic adsorbent" is defined as a zeolite or a zeolite-related material having cavities of which the dimensions are larger than the pore openings giving access to these cavities. The term "cavities" of the zeolitic adsorbent, as used herein refers to regions of expanded spaciousness such as but not limited to internal cavities, cages, supercages, lobes, channel intersections, side pockets, etc. . . . These cavities have larger dimensions than the pore openings giving access to these cavities. Preferably these cavities have a smallest diameter of at least 4.5 Angström and a largest diameter of at least 10 Angström. More preferably said cavities have a smallest diameter between 4.5 and 15 Angström and a largest diameter between 10 and 25 Angström.

Non-limiting examples of such zeolite or zeolite-related materials are materials with structure type MWW (e.g. MCM-22, SSZ-25, ERB-1, PSH-3, ITQ-1), IFR (e.g. SSZ-42, MCM-58, ITQ-4), LTL (e.g. L, [Al—P—O]-LTL, Gallosilicate L, LZ-212, Perlialite), CLO (e.g. Cloverite, [Mn—Ga—P—O]-CLO, [Zn—Ga—P—O]-CLO) or CON (e.g. CIT-1, SSZ-26, SSZ-33).

In a preferred embodiment, said zeolitic adsorbent is a zeolite with structure type MWW. Zeolites with structure type MWW have a non-interconnected two-dimensional network. One of the pore networks is constituted by 10 MR (member rings) channels, and the second is constituted by 12 MR channels connected together via 10 MR channels, such that access to the 12 MR channels is only via 10 MR channels. However, any other zeolitic adsorbent with principal channels with the opening defined by a ring of 10 oxygen atoms and secondary channels with an opening defined by a ring with more than 12 oxygen atoms is suitable for carrying out the process of the invention.

In a preferred embodiment, the zeolitic adsorbent used according to the present invention is a crystalline material having a composition involving the molar relationship:

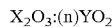

wherein X is a trivalent element, such as aluminum, boron, iron and/or gallium, preferably aluminum, Y is a tetravalent element such as silicon and/or germanium, preferably silicon, and n is at least 2, and usually more than 10, more usually more than 20.

In another preferred embodiment, the zeolitic adsorbents used to carry out the process of the invention advantageously contain silicon and at least one element X selected from the group formed by aluminum, iron, gallium and boron, preferably aluminum. The silica content in these adsorbents can vary. Preferably, the Si/X mole ratio is at least 5.

In another embodiment, in the as-synthesized form, the zeolitic adsorbent used according to the present invention has a formula, on an anhydrous basis and in terms of moles of oxides per n moles of $YO_2$, as follows:

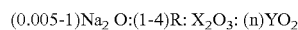

wherein R is an organic moiety. The Na and R components are associated with the zeolitic adsorbent as a result of their presence during crystallization, and are easily removed by post-crystallization methods.

The zeolitic adsorbent used according to the present invention is thermally stable and exhibits high surface area (greater than 400 $m^2/gm$). To the extent desired, however, the original sodium cations of the as-synthesized material can be replaced in accordance with techniques well known in the art, at least in part, by ion exchange with other cations. Preferred replacing cations include metal ions, hydrogen ions, hydrogen precursor, e.g. ammonium, ions and mixtures thereof. Particularly preferred cations are those which tailor the catalytic activity for certain hydrocarbon conversion reactions. These include hydrogen, rare earth metals and metals of Groups IIA, IIIA, IVA, IB, IIB, IIIB, IVB and VIII of the Periodic Table of the Elements.

In a more preferred embodiment, said zeolitic adsorbent is MCM-22. The MCM-22 structure has several interesting features. It is known to possess two independent, non-interconnecting, 2-dimensional pore systems. The first pore system is defined by two-dimensional sinusoidal channels, which maintain an effective 10-ring diameter throughout the structure, accessible through 10 ring apertures of 0.40×0.59 nm. The second pore system consists of large 12-member ring egg-shaped supercages with an inner free diameter of 0.71 nm and height of 1.82 nm interconnected by 10-member ring pore openings. The supercages are accessible via 10 ring apertures of 0.40×0.54 nm. Structure and synthesis of zeolite MCM-22 was reported in U.S. Pat. No. 4,954,325, the disclosures of which is incorporated by reference into the present specification.

In accordance with the invention, the zeolitic adsorbents as defined in the present invention preferably adsorb mono-branched alkanes, to lesser extent linear alkanes and only minor amounts of multi-branched alkanes.

The separation process of the present invention can employ adsorption separation techniques that are well known to the skilled person, such as PSA (pressure swing adsorption), TSA (temperature swing adsorption), membrane based separation processes, and chromatographic processes, e.g. simulated moving bed or elution chromatography or a combination of those techniques. The separation process of the invention can also be operated in the liquid phase or in the gas phase.

It was demonstrated that the selective uptake of mono-branched alkanes from mixtures with linear and multi-branched alkanes occurs at low, intermediate and high pore occupancy. The term "pore occupancy", as used herein, refers to the amount of pores of the zeolitic material that is filled up with hydrocarbon molecules.

The term "low pore occupancy" refers to an amount of pores of the zeolitic material that is comprised between 0.01 and 25%, and preferably between 0.01 and 15% that is filled up with hydrocarbon molecules.

The term "intermediate pore occupancy" refers to an amount of pores of the zeolitic material that is comprised between 26 and 75%, and preferably between 40 and 60% that is filled up with hydrocarbon molecules.

The term "high pore occupancy" refers to an amount of pores of the zeolitic material that are filled up with hydrocarbon molecules which is comprised between 75 and 100% and preferably between 85 and 100%.

In a preferred embodiment, the invention thus relates to a method for separating mono-branched alkanes from a mixture of alkanes and to a method for separating a mixture of hydrocarbons, preferably alkanes, into fractions enriched in linear, mono-branched, or multi-branched hydrocarbons, preferably alkanes, whereby said zeolitic adsorbent has a pore occupancy comprised between 0.01 and 100%.

In another embodiment, the invention provides a method for separating mono-branched alkanes from mixtures of n-alkanes and mono-branched alkanes, such as butane/iso-butane or pentane/isopentane mixtures. Feeding such mixtures to an adsorption column filled with a zeolitic adsorbent will deliver an effluent stream enriched in linear alkanes, and the mono-branched alkanes will be enriched in the pores of the adsorbent. A stream enriched in mono-branched alkanes is obtained by desorbing the adsorbed mono-branched alkanes using a suitable technique such as but not limited to pressure or temperature swing, desorption with a suitable desorbent or a combination of these.

In another preferred embodiment, the mixture wherefrom the mono-branched hydrocarbons, preferably alkanes, are separated according to the invention is a mixture of linear, mono-branched and multi-branched alkanes. Preferably, said mixture comprises 0.1-99.9%, preferably 20-99.9%, linear alkanes, and 0.1-99.9%, preferably 0.1-70%, mono-branched alkanes and 0.1-90%, preferably 20-60%, multi-branched alkanes.

In an example, the feeds separated according to the present invention are paraffinic in nature, and contain 4 to 8 carbon atoms per molecule. Said feedstocks consist of butane, pentane, hexane, heptane or octane fractions (including linear alkanes as well as alkane isomers), or any combination of these. These feedstocks are obtained via distillation of crude oil, via isomerization processes (light naphtha isomerization, butane isomerization), via reforming processes or via any other conversion process in which alkanes are formed or converted. Besides paraffins, these feedstocks can also contain naphtenic, aromatic or olefinic compounds.

In another preferred embodiment, the mixture of alkanes is a mixture of linear and mono-branched alkanes in a ratio comprised between 1:100 to 100:1, and preferably 1:50 to 50:1 and more preferably 1:30 to 30:1. In a most preferred embodiment, the mixture comprises mono-branched and linear alkanes in a ratio of 1:1.

In a preferred example, a mixture of n-butane and iso-butane is separated according to the present invention into a fraction enriched in iso-butane and a fraction enriched in n-butane by contacting this mixture with an adsorbent having a higher selectivity for iso-butane than for n-butane. In a more preferred embodiment said mixture is contacted with zeolite MCM-22.

According to yet another preferred embodiment, the separation method according to the present invention is based on entropic effects.

"Entropy" is to be considered as a measure of disorder or randomness. Highly disordered system is said to have a high entropy. When a molecule transforms from a bulk state (e.g. gas, liquid state) to an adsorbed state, it looses at least one degree of freedom, and entropy is thus decreased (less disorder).

The term "enthalpy" refers to the energetic interaction between materials and molecules. Enthalpy is the heat liberated or adsorbed by chemical reactions that are conducted under constant pressure.

In general, for adsorption of homologous hydrocarbon series on zeolites, a linear relationship between these two thermodynamic properties exists, which is known as the iso-equilibrium or compensation effect (Eder, F.; Lercher, J. A., "On the role of the pore size and tortuosity for sorption of alkanes in molecular sieves", *J. Phys. Chem. B*, 101, 1273-1278 (1997).). The adsorption enthalpy increases almost linearly with carbon number as a result of the additive character of dispersion forces governing the energetic interaction between the highly non-polar alkanes and the zeolites' framework. More tightly adsorbed molecules loose more freedom, explaining the linear relationship between adsorption enthalpy and entropy or $\ln(K_0)$ (Ocakoglu, A. R., Denayer, J. F. M., Marin, G. B., Martens, J. A., Baron, G. V., Tracer Chromatographic Study of Pore and Pore Mouth Adsorption of Linear and Monobranched Alkanes on ZSM-22 Zeolite, J. Phys. Chem. B, 207, 398-406, 2003.).

Generally, it is observed that branched alkanes adsorbed in the pores of the zeolitic material loose more freedom compared to linear alkanes since these more bulky branched molecules are more constrained by the narrow pores of the zeolitic material compared to the linear alkanes. However, according to the present invention, an inverse mechanism is observed. The mono-branched alkanes loose less freedom upon adsorption on the zeolites and have a combination of adsorption entropy and enthalpy which gives them a Gibbs adsorption energy favoring their adsorption compared to their linear isomers.

The present invention further relates to the use of at least one adsorbent, preferably a zeolitic adsorbent as defined herein, for separating a mixture e.g. of hydrocarbons, preferably of alkanes, into fractions enriched in linear, mono-branched, or multi-branched hydrocarbons, preferably alkanes. Preferably, the invention relates to the use of at least one adsorbent, said adsorbent being as defined herein, for preferentially adsorbing mono-branched hydrocarbons, and preferably alkanes, e.g. from a mixture of hydrocarbons, and preferably of alkanes, said mixture being as defined herein. Separation is based on entropic effects as explained above.

The zeolitic adsorbents as described above can be effectively used in multiple applications wherein the selective adsorption and separation of mono-branched alkanes is desired, for instance for the separation of butane/iso-butane, the purification of butane containing trace amounts of iso-butane by selective adsorption of iso-butane, separation of linear and branched C5/C6 alkane fractions, separation of light naphtha fractions, separation of butene/iso-butene cuts, separation of mixtures of linear and branched olefins in the C5-C7 range, butene isomerization processes, butene alkylation processes, etc. . . .

The zeolites described in this invention can also be used in combination with a catalyst to produce specific mixtures of hydrocarbons by conversion over the catalyst followed by separation over a zeolite adsorbent into a product stream and a stream for recycling to the catalyst. Adsorptive reactors could utilize the separation principle described herein with catalytic conversion in a single unit. A possible example is the use of MCM-22 in the isomerization of butane into iso-butane, to increase the iso-butane yield. This is achieved by using a C4 isomerization catalyst with an MCM-22 adsorbent in any of the known types of reactor or reactor-separator, such that the iso-butane molecules formed in the catalytic reactions are removed from the reaction mixture by selective adsorption on MCM-22, shifting the thermodynamical equilibrium in favor of iso-butane formation, resulting in a higher degree of conversion and iso-butane yield.

In another embodiment the invention relates to the use of MCM22 as a zeolite having a catalytic and an adsorbent activity.

The ability of a molecule to rotate in a cage can be estimated by comparing the radius of gyration of its van der Waals volume, $R_g$, assuming rotation around the centre of mass, to the radius $R_c$ of the largest sphere that fits into the van der Waals contour of the cage or pore. Minimal rotational entropy loss is combined with maximal energetic interactions when the sphere circumscribing the rotational motion of the molecule matches with the internal surface of the cage, i.e. when the radius ratio $R_g/R_c$ equals unity.

The equilibrium adsorption properties of linear and branched alkanes on zeolites with cages or tubular pores were determined. Iso-alkanes, with their shorter main carbon chain, have a smaller radius of gyration and a more sphere-like shape than their linear isomers. This rotates more easily in zeolite cages, what leads to their preferential adsorption.

Herein, molecular separation, based on differences in molecular rotation in zeolite cages is introduced. Rotational entropy driven separation can be useful in the separation of structural isomers, such as n- and iso-alkanes, aromatic compounds or other mixtures of differently shaped molecules.

The present invention will now be described with reference to clarifying examples that can by no means be limiting the protection of the invention.

EXAMPLES

Example 1

In this example pulse chromatographic measurements were performed with a series of zeolites with widely different pore structure and architecture to study shape selectivity in the adsorption of n- and iso-alkanes.

The chromatographic experiments were preformed in a HP 4890 gas chromatograph. Linearity of the experiments was confirmed by injecting different amounts and using different carrier flow rates. Detailed explanation of the experimental set-up and procedure can be found in Ocakoglu et al, 2003 (J. Phys. Chem. B, 207, 398-406). Henry adsorption constants were calculated from the first moment of the chromatographic response curves [Ruthven, D. M., Principles of adsorption and adsorption processes; John Wiley and Sons: Canada, 1984.] Applied zeolites comprised MCM-022, beta, mordenite, ZSM-5 and ZSM-22.

Figure 1:
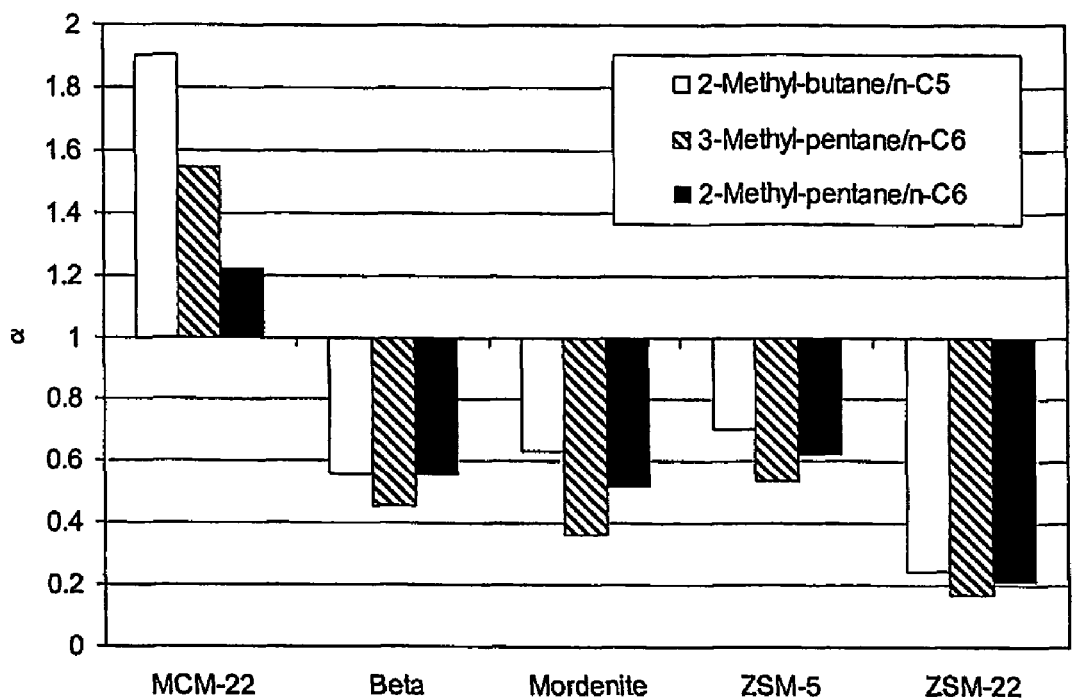
FIG. 1 shows the ratio of low coverage adsorption constants α of linear and mono-branched alkanes on different zeolites at 300° C.

FIG. 1 shows the ratio of low coverage Henry adsorption constants α of mono-branched and linear alkanes being 2-methylbutane, 2-methylpentane and 3-methylpentane on MCM-22, Beta, mordenite, ZSM-5 and ZSM-22 at 300° C. Zeolites Beta, mordenite, ZSM-5 and ZSM-22 (with smaller pore sizes, ranging between 4.5 and 7.5 Angstrom), all prefer the linear alkanes, and selectivities α around or lower than 0.5 are obtained. With the latter materials, steric constraints disfavor adsorption of iso-alkanes, a tendency in agreement with classical shape selectivity concepts. However, a peculiar behavior is observed with MCM-22, showing a pronounced selectivity for the more bulky (mono-branched) isomer. For example, the Henry adsorption constant of 2-methylbutane is 1.9 times larger than that of pentane at 300° C.

Figure 2:
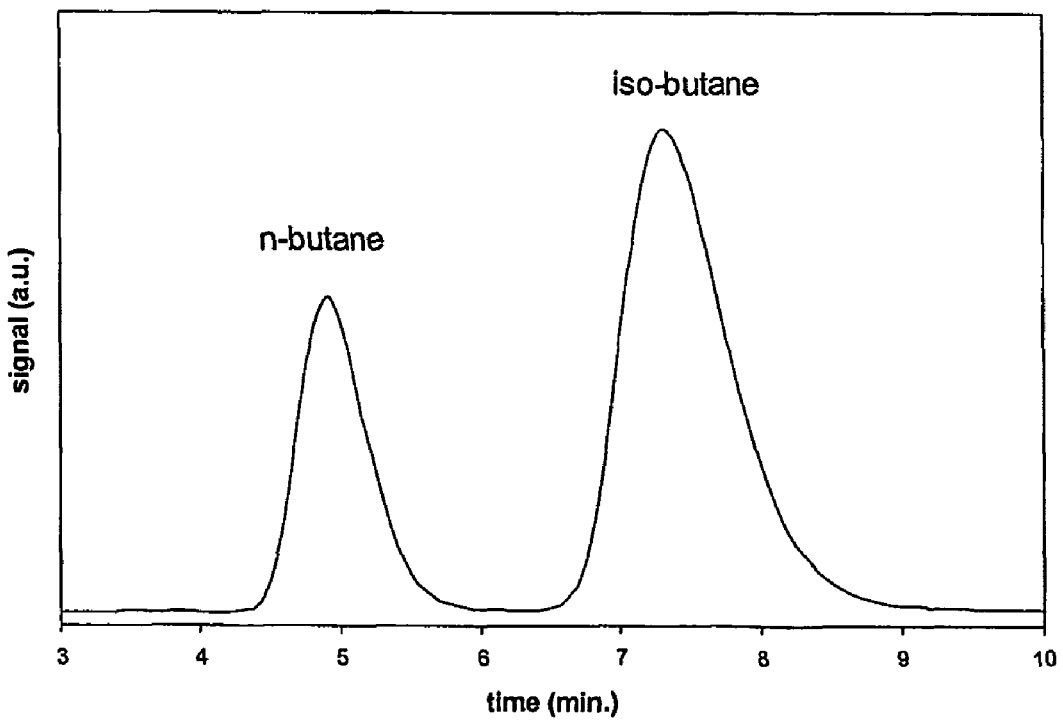
FIG. 2 illustrates the separation of butane and iso-butane on MCM-22 at 200° C.
Figure 3:
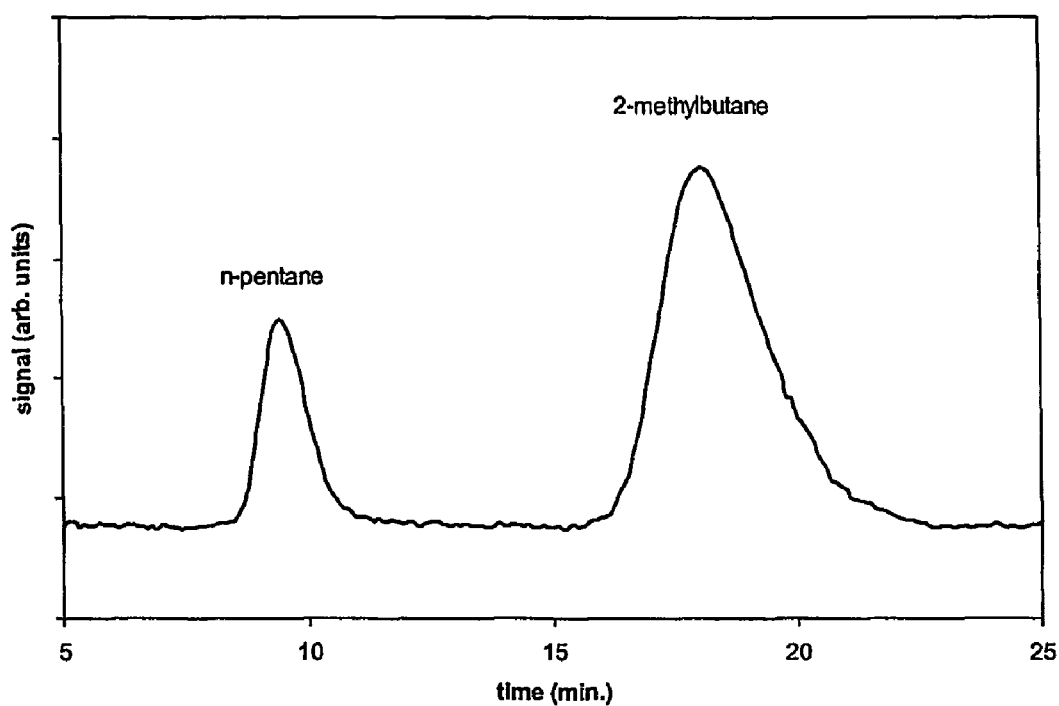
FIG. 3 illustrates the separation of pentane and 2-methylbutane on MCM-22 at 200° C.
Figure 4:
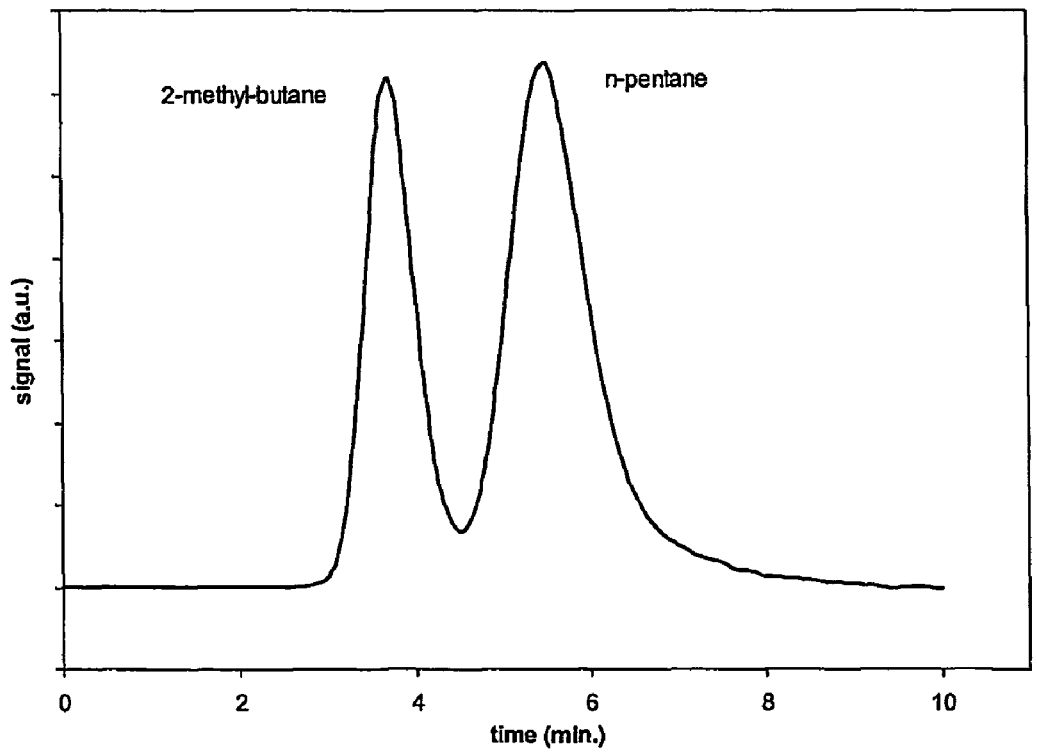
FIG. 4 illustrates the separation of pentane and 2-methylbutane on mordenite at 200° C.

Chromatograms obtained from injection of equimolar mixtures of butane/isobutane and pentane/2-methylbutane mixture into columns (with a length of 70 cm) packed with zeolite MCM-22, are depicted in FIGS. 2 and 3 respectively. The observed order of elution with MCM-22, namely higher retention of the bulkier mono-branched molecule compared to its linear counterpart, is the first example of a separation showing inverse shape selectivity at very low occupancy. Both components are very well separated on a column of only 70 cm. In contrast, with Mordenite (FIG. 4), Beta, ZSM-5 and ZSM-22, the linear alkane molecule retains longer at low zeolite loading, as expected for conventional shape-selective zeolites.

Figure 5:
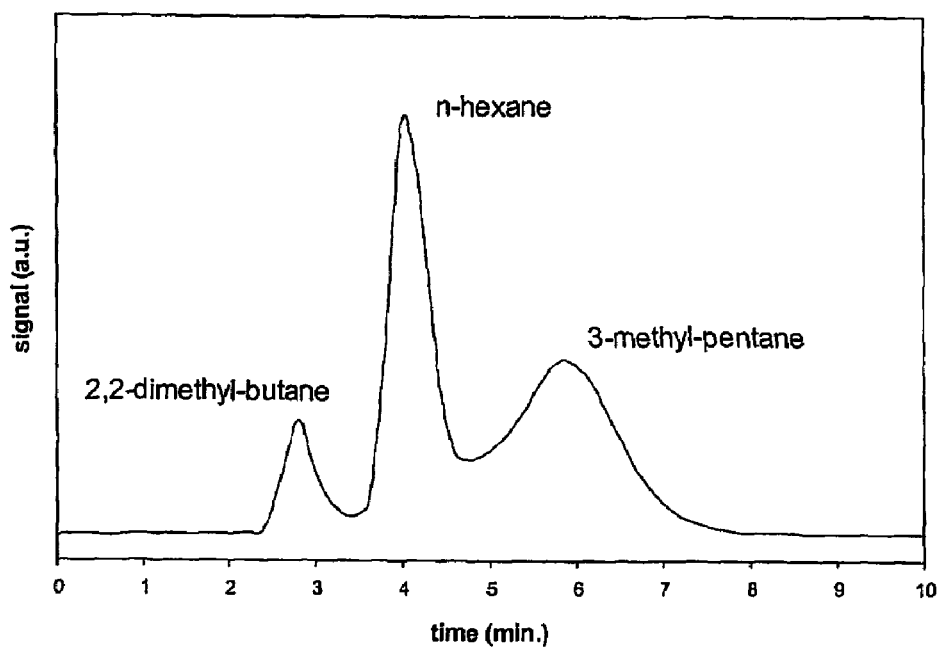
FIG. 5 illustrates the separation of 2,2-dimethyl-butane, n-hexane and 3-methyl-pentane on MCM-22 at 200° C.

In FIG. 5, the chromatogram obtained after injection of a mixture of 2,2-dimethylbutane, n-hexane and 3-methylpentane in a column packed with MCM-22 is depicted. The di-branched molecule 2,2-dimethylbutane elutes first as the selectivity of MCM-22 for this molecule is very low. 3-methylpentane is the most strongly retained, and n-hexane elutes between the mono-branched and the di-branched molecules.

Table 1 gives the ratio of Henry adsorption constants of some selected hexane isomers to the Hemy constant of n-hexane. Obviously, mono-branched hexanes have a higher Henry constant than n-hexane, and di-branched hexane isomers have a lower Henry constant than n-hexane.

TABLE 1

| ratio of Henry constants on MCM-22 at 250° C. | |
|---|---|
| K' 2-methylpentane/K' n-hexane | 1.2 |
| K' 3-methylpentane/K' n-hexane | 1.5 |
| K' 2,2-dimethylbutane/K' n-hexane | 0.7 |
| K' 2,3-dimethylbutane/K' n-hexane | 0.8 |

Figure 6:
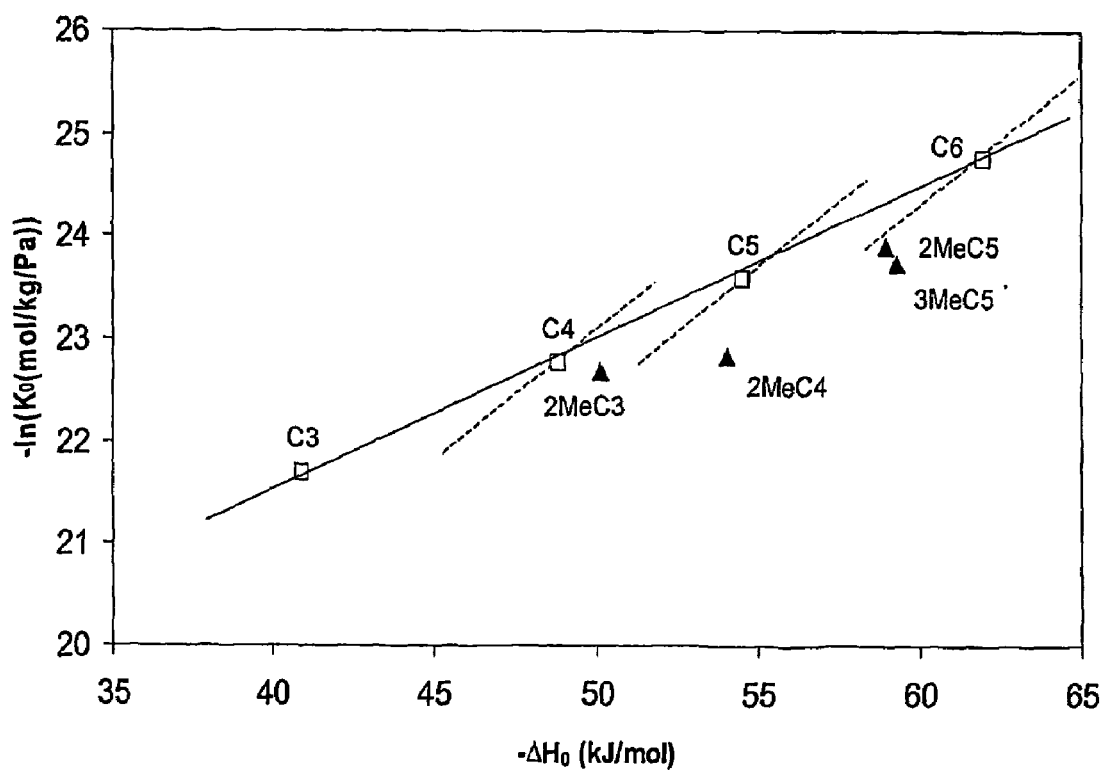
FIG. 6 shows a compensation plot between adsorption entropy and enthalpy for MCM-22.

The low coverage adsorption behavior is governed by Henry's law constant, being temperature dependent and following the van't Hoff equation, including an adsorption enthalpy term and a pre-exponential adsorption entropy related term $K_0$ ($\ln(K_0) \approx \Delta S_0$) (Ocakoglu, A. R., Denayer, J. F. M., Marin, G. B., Martens, J. A., Baron, G. V., Tracer Chromatographic Study of Pore and Pore Mouth Adsorption of Linear and Monobranched Alkanes on ZSM-22 Zeolite, J. Phys. Chem. B, 207, 398-406, 2003.). For adsorption of homologous hydrocarbon series on zeolites, a linear relationship between these two thermodynamic properties exists, which is known as the iso-equilibrium or compensation effect. Such compensation between adsorption entropy and enthalpy is also observed for C3-C6 n-alkanes with zeolite MCM-22 (FIG. 6). The adsorption enthalpy increases almost linearly with carbon number as a result of the additive character of dispersion forces governing the energetic interaction between the highly non-polar alkanes and the zeolites' framework. More tightly adsorbed molecules loose more freedom, explaining the linear relationship between adsorption enthalpy and entropy or $\ln(K_0)$. For a branched molecule to have a higher Henry adsorption constant than its linear isomer, it needs to have a combination of adsorption enthalpy and entropy resulting in a lower Gibbs free energy of adsorption. Knowing the relationship between $\ln(K_0)$ and the adsorption enthalpy for linear alkanes, a criterion for $\ln(K_0)$ and $\Delta H_0$ of the branched molecules can be calculated which should be fulfilled to obtain inverse shape selectivity. In fact, this criterion is expressed as a line, crossing the compensation point of the linear alkane and dividing the $\ln(K_0)$ versus $\Delta H_0$ plane into two parts (depicted by the dotted lines in FIG. 6). Molecules having a combination of $\ln(K_0)$ and $\Delta H_0$ lying below this line have a lower Gibbs free energy of adsorption and thus a higher adsorption constant.

All mono-branched alkanes lie in the zones of preferred adsorption with MCM-22. Compared to butane, isobutane has a slightly higher adsorption enthalpy (C4: 48.8 kJ/mol; isoC4: 50.1 kJ/mol), which can be explained by a better agreement between the shape of isobutane and the pores of MCM-22. Moreover, isobutane has a less negative $\ln(K_0)$, meaning that this molecule looses less freedom upon adsorption compared to its linear isomer, although it is more strongly adsorbed. 2-Methylbutane, 2-methylpentane and 3-methylpentane have lower adsorption enthalpies than their linear isomers, but are adsorbed preferentially as they loose much less freedom in the adsorbed state. For example, the entropy loss of 3-methylpentane is 8.3 J/mol/K lower than that of hexane. Such a behavior is completely unexpected and can be attributed to the peculiar structure of MCM-22, having two independent pore systems (Lawton et al. 1998; 23:109-117). The first pore system is defined by two-dimensional sinusoidal channels, which maintain an effective 10-ring diameter throughout the structure, accessible through 10 ring apertures of 0.40×0.59 nm. The second one consists of large supercages with an inner free diameter of 0.71 nm and height of 1.82 nm. The supercages are accessible via 10 ring apertures of 0.40× 0.54 nm. The very peculiar adsorption behavior is ascribed to the unique shape of the supercages, which are very well accommodating the mono-branched alkanes, in such a way that they retain more freedom than the linear isomers.

Example 2

In addition to the pulse experiments in the Henry region, at infinite dilution, pulse chromatographic experiments were performed with a mixture of Helium/iso-butane as carrier gas to preload MCM-22 with iso-butane molecules in order to investigate whether the observed inversion of adsorption selectivity is restricted to low coverage, where adsorbed molecules are isolated from each other. Injection of hexane/3-methylpentane and hexane/3-methylpentane mixtures in a column filled with MCM-22 and preloaded with iso-butane gave even higher selectivities towards the mono-branched alkanes as compared to measurements at 0% pore filing in the Henry region, as shown in Table 2.

TABLE 2

Ratio of first moments of response curves of n-hexane, 2-methylpentane and 3-methylpentane at 0% of pore filling and at 60% zeolite pore filling (at 200° C.)

| Zeolite loading | μ 3-methylpentane/ μ n-hexane | μ 2-methylpentane/ μ n-hexane |
|---|---|---|
| 0% | 1.4 | 1.2 |
| 60% | 1.6 | 1.3 |

Example 3

From a practical point of view, it is at utmost interest to study the adsorption also at full zeolite loadings in liquid phase, as real processes are performed at high concentrations or pressure. Liquid phase experiments were performed as follows: a typical amount of 0.4 g of fresh zeolite contained in a 10 ml vial was regenerated in a GC oven at 450° C. during 12 hours and at the end of the regeneration it was sealed immediately. The amount of zeolite was measured with a calibrated Ohaus Explorer balance before and after regeneration in order to determine the weight amount of zeolite. As non-adsorbing solvent 2, 2, 4-trimethylpentane (iso-octane, 99.5% purity, Acros) was used. Solutions of iso-octane and adsorbates of interest were prepared in 20 ml vials. The concentration of iso-octane was approximately 99.5 weight % in each case and the rest included the adsorbate(s). About 12 ml of this solution was extracted and partitioned into the vial containing the regenerated zeolite (about 10 ml) and into an empty 2 ml vial for the determination of the initial concentrations, this latter was analyzed immediately. The vials with zeolite were kept at 4° C. for equilibration during two days. After the equilibration period, samples from the liquid phase were extracted and analyzed in order to obtain the final concentrations in the liquid phase. The amounts adsorbed were then determined from the difference between initial and final concentrations. Surprisingly the same striking adsorption behavior of zeolite MCM-22 is maintained in liquid phase where the pores of zeolite MCM-22 are totally filled up with hydrocarbon molecules. This is shown in FIG. 7, giving the selectivity diagram for the liquid phase adsorption of pentane/2-methylbutane mixtures. The separation factor α between 2-methylbutane and pentane for this liquid phase experiment at room temperature is lower than in the Henry region at temperatures between 150 and 250° C. (1.4 compared to 1.9). When the pores are completely filled, steric constraints become more important and reduce the advantage of the branched molecules.

In conclusion, the present example illustrates that zeolite MCM-22 allows to reverse the "normal" adsorption selectivity between linear and mono-branched alkanes. This zeolite shows a pronounced selectivity for the more bulky, mono-branched alkanes, at low, intermediate and high pore occupancy. This unique feature may have significant consequences for processes dealing with mixtures of n- and iso-alkanes, e.g. separation of butane/iso-butane, separation of linear and branched C5/C6 alkane fraction, butene isomerization processes, butene alkylation processes, etc. . . .

Example 4

This example illustrates the separation of a mixture of alkanes into fractions of linear, mono-branched and multi-branched alkanes by applying a method according to the present invention.

When a mixture of linear, mono-branched and multi-branched alkanes is introduced into a simulated moving bed containing MCM-22 adsorbent, a raffinate stream enriched in multi-branched alkanes is removed from the simulated moving bed, as these multi-branched compounds are nearly not adsorbed by MCM-22. The n-alkanes adsorbed by the MCM-22 adsorbent can then be desorbed using a first desorbent, incapable of desorbing the mono-branched alkanes, such that a stream enriched in n-alkanes is obtained. The mono-branched alkanes are than desorbed using another desorbent, such that a stream enriched in mono-branched alkanes is obtained. Preferably, the n-alkanes are first desorbed using an n-alkane fraction, e.g. pentane, and subsequently, the mono-branched alkanes are desorbed using a fraction enriched in mono-branched alkanes, e.g. 2-methyl-butane.

Example 5

This example further illustrates the preferential adsorption of mono-branched hydrocarbons from a mixture of hydrocarbons by applying a method according to the present invention.

By exploiting rotational entropy effects, separation patterns different from those found typically can be obtained. Column breakthrough experiments were performed in which equimolar butane/isobutane and pentane/2-methyl-butane mixtures diluted in Helium as inert gas were separated on an adsorption column packed with MCM-22. The total partial hydrocarbon pressure was equal to 0.2 bar in both cases. The length of the adsorption column was 0.7 m. FIGS. 8 and 9 show breakthrough profiles for butane/isobutane and pentane/2-methylbutane mixtures separated on an MCM-22 column. Also in these conditions where the MCM-22 pores were saturated with molecules, the components were very well separated. In both cases, the linear alkane eluted first, followed by the branched chain, demonstrating the preference of MCM-22 for adsorbing monobranched alkanes over their linear isomers.

What is claimed is:

1. A method for separating mono-branched hydrocarbons from a mixture of hydrocarbons comprising:
bringing said mixture into contact with one adsorbent having a selectivity order from mono-branched to linear further to multi-branched hydrocarbons,
preferentially and selectively adsorbing said mono-branched hydrocarbons by said adsorbent, and
desorbing said mono-branched hydrocarbons from said adsorbent, thereby selectively separating said mono-branched hydrocarbons.

2. The method according to claim 1 comprising the step of bringing said mixture into contact with only one absorbent.

3. The method according to claim 1, wherein said hydrocarbons are alkanes.

4. The method according to claim 3 wherein said mixture of alkanes is a mixture selected from linear, mono-branched and multi-branched alkanes.

5. The method according to claim 4, wherein said mixture comprises 0.1-99.9% linear, 0.1-99.9% mono-branched and 0.1-90% multi-branched alkanes.

6. The method according to claim 4, wherein said mixture of alkanes is a mixture of linear and mono-branched alkanes in a ratio comprised between 1:100 to 100:1.

7. The method according to claim 6, wherein said mixture comprises mono-branched and linear alkanes in a ratio of 1:1.

8. The method according to claim 1, wherein said adsorbent is a zeolitic adsorbent.

9. The method according to claim 8, wherein said zeolitic adsorbent comprises the molar relationship

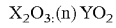

wherein n is at least 2, X is a trivalent element and Y is a tetravalent element.

10. The method according to claim 9, wherein n is at least 2, wherein X is selected from the group consisting of aluminum, iron, gallium and boron and wherein Y is silicon.

11. The method according to claim 9, wherein n is at least 10, wherein X is aluminum, and wherein Y is silicon.

12. The method according to claim 8, wherein said zeolitic adsorbent is MCM- 22.

13. The method according to claim 8, wherein said zeolitic adsorbent has a pore occupancy comprised between 0.01 and 100%.

14. The method according to claim 1, wherein said adsorbent is a zeolitic adsorbent having cavities of which the dimensions are larger than the pore openings giving access to said cavities, these cavities having a smallest diameter of at least 4.5 Angström and a largest diameter of at least 10 Angström.

15. The method according to claim 14, wherein said cavities have a smallest diameter between 4.5 and 15 Angström, and a largest diameter between 10 and 25 Angström.

16. The method according to claim 1, wherein said separation is based on entropic effects.

17. A method for separating mixtures of hydrocarbons into fractions of linear, mono- branched and multi-branched hydrocarbons comprising the steps of:
a. bringing said mixture into contact with only one adsorbent, said adsorbent having a selectivity order from mono-branched to linear further to multi-branched hydrocarbons,
b. separating a stream enriched in multi-branched hydrocarbons from said adsorbent, thereby separating said multi-branched hydrocarbons,
c. desorbing the linear hydrocarbons from said adsorbent, thereby separating said linear hydrocarbons, and
d. desorbing said mono-branched hydrocarbons from said adsorbent, thereby separating said mono-branched hydrocarbons.

18. A method for separating mono-branched hydrocarbons from a mixture of hydrocarbons consisting of linear, mono-branched, and multi-branched alkanes which comprises bringing said mixture of hydrocarbons into contact with only one zeolitic adsorbent, wherein mono-branched alkanes from said mixture are preferentially absorbed.

19. The method according to claim 18, wherein said separation is based on entropic effects.

20. The method according to claim 18, wherein said one zeolitic adsorbent is MCM-22 as a zeolite having a catalytic and an adsorbent activity.

* * * * *

UNITED STATES PATENT AND TRADEMARK OFFICE
CERTIFICATE OF CORRECTION

PATENT NO. : 7,435,865 B2  Page 1 of 1
APPLICATION NO. : 10/568723
DATED : October 14, 2008
INVENTOR(S) : Denayer et al.

It is certified that error appears in the above-identified patent and that said Letters Patent is hereby corrected as shown below:

Column 6, Lines 14, "2-metylpentane," should be changed to --2-methylpentane,--

Column 6, Lines 15-16, "4-ethylheptane," should be changed to --4-methylheptane,--

Column 9, Line 34, "naphtenic, aromatic" should be changed to --naphthenic, aromatic--

Column 12, Line 7, "to the Hemy" should be changed to --to the Henry--

Column 15, Line 13, "only one absorbent." should be changed to --only one adsorbent.--

Column 15, Line 24, "between 1:100to 100:1." should be changed to --1:100 to 100:1.--

Column 15, Line 32, "$X_2O_3:(n)YO_2$" should be changed to --$X_2O_3:(n)YO_2.$--

Column 15, Line 42, "is MCM- 22." should be changed to --is MCM-22.--

Column 16, Line 4, "claim 1,wherein" should be changed to --claim 1, wherein--

Column 16, Line 16, "mono- branched and" should be changed to --mono-branched and--

Signed and Sealed this

Seventeenth Day of March, 2009

JOHN DOLL
*Acting Director of the United States Patent and Trademark Office*